United States Patent
Pirot et al.

(10) Patent No.: US 9,989,478 B2
(45) Date of Patent: Jun. 5, 2018

(54) METHOD AND DEVICE FOR INSPECTING PACKAGING WELDS

(71) Applicant: BIZERBA LUCEO, Vern-sur-Seiche (FR)

(72) Inventors: Eric Pirot, Cesson Sevigne (FR); Laurent Roubert, Boug des Comptes (FR); Ahmed Rbaa, Rennes (FR)

(73) Assignee: BIZERBA LUCEO, Vern-sur-Seiche (FR)

( * ) Notice: Subject to any disclaimer, the term of this patent is extended or adjusted under 35 U.S.C. 154(b) by 62 days.

(21) Appl. No.: 15/023,078

(22) PCT Filed: Oct. 9, 2014

(86) PCT No.: PCT/FR2014/052566
§ 371 (c)(1),
(2) Date: Mar. 18, 2016

(87) PCT Pub. No.: WO2015/052445
PCT Pub. Date: Apr. 16, 2015

(65) Prior Publication Data
US 2016/0231254 A1    Aug. 11, 2016

(30) Foreign Application Priority Data
Oct. 11, 2013    (FR) ...................... 13 59920

(51) Int. Cl.
*G01N 21/88*    (2006.01)
*G01N 21/90*    (2006.01)
*G01N 21/95*    (2006.01)

(52) U.S. Cl.
CPC ..... *G01N 21/9054* (2013.01); *G01N 21/8851* (2013.01); *G01N 21/95* (2013.01); *G01N 2021/8887* (2013.01); *G01N 2201/105* (2013.01)

(58) Field of Classification Search
CPC ........... G01N 21/8851; G01N 21/9054; G01N 21/95; G01N 2021/8887; G01N 2201/105
See application file for complete search history.

(56) References Cited

U.S. PATENT DOCUMENTS

| 5,515,159 A | 5/1996 | Sites et al. | |
| 5,533,146 A * | 7/1996 | Iwai | B23K 9/0956 219/121.63 |

(Continued)

FOREIGN PATENT DOCUMENTS

| FR | 2 744 422 | 8/1997 |
| FR | 2 855 268 | 11/2004 |

(Continued)

OTHER PUBLICATIONS

Lenzi et al. ("Inspection of laser-seam welds in automobile manufacturing," SPIE vol. 5782, Mar. 28, 2005).*

(Continued)

*Primary Examiner* — Yubin Hung
(74) *Attorney, Agent, or Firm* — Clark & Brody

(57) ABSTRACT

A method of inspecting packaging welds comprises the steps of creating a light beam that produces at least one light transition (t) and acquiring a raw matrix image (B(N)) covering the light transition. For each image (B(N)) obtained, a measurement of the diffusion of the light transition is stored. For each of N successive scanning increments, the raw matrix image (B(N)) is used to create an image line in which each pixel receives as its value the measurement in the raw matrix image (B(N)) of the diffusion of at least the light transition. The at least N image lines are stored in succession to obtain a matrix image and the matrix image is analyzed to determine that the weld along said fraction is in conformity when its transverse width remains, at all points, greater than a given minimum.

22 Claims, 4 Drawing Sheets

(56) References Cited

U.S. PATENT DOCUMENTS

| | | | | |
|---|---|---|---|---|
| 5,621,811 | A * | 4/1997 | Roder | G01N 23/043 348/126 |
| 2005/0041781 | A1 * | 2/2005 | Jefferson | G06T 11/006 378/210 |
| 2005/0050451 | A1 | 3/2005 | Abdollahi et al. | |
| 2005/0147289 | A1 * | 7/2005 | Kodama | B21C 37/0811 382/152 |
| 2011/0262007 | A1 * | 10/2011 | Kojima | G01B 11/2509 382/103 |
| 2012/0234805 | A1 * | 9/2012 | Schwarz | B23K 26/03 219/121.63 |
| 2013/0094875 | A1 * | 4/2013 | Ogata | H04N 5/335 399/74 |
| 2014/0146169 | A1 * | 5/2014 | Ollivier | G01N 21/88 348/131 |

FOREIGN PATENT DOCUMENTS

| | | |
|---|---|---|
| FR | 2 907 424 | 4/2008 |
| WO | 2010/052431 | 5/2010 |
| WO | 2013/007951 | 1/2013 |

OTHER PUBLICATIONS

Liu et al. ("Study on visual image information detection of external angle weld based on arc welding robot," SPIE vol. 7513, Nov. 24, 2009).*

Zhang et al. ("Simultaneous vision image sensing of weld pool of pulsed GTAW in multi-orientation in a frame," SPIE vol. 4553, Sep. 25, 2001).*

* cited by examiner

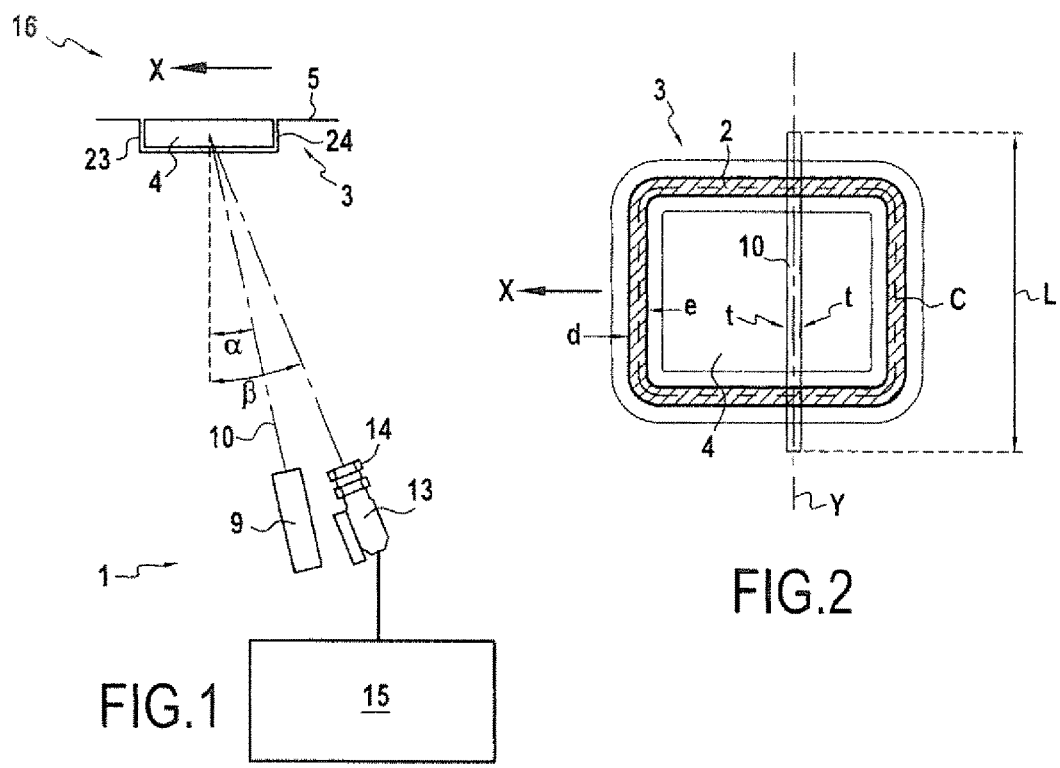
FIG.1
FIG.2
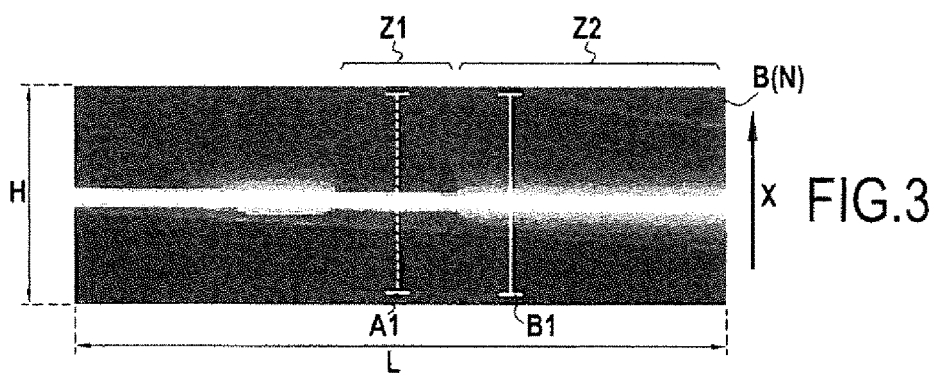
FIG.3
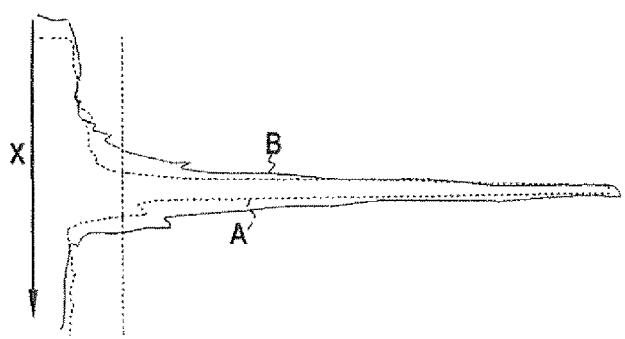
FIG.3A

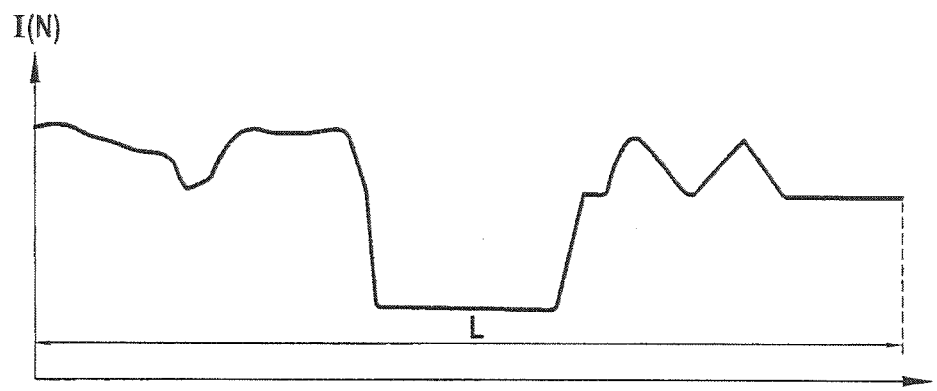
FIG.6
FIG.7A
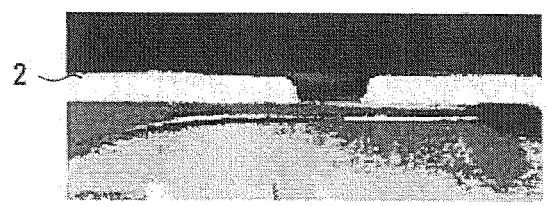
FIG.7B
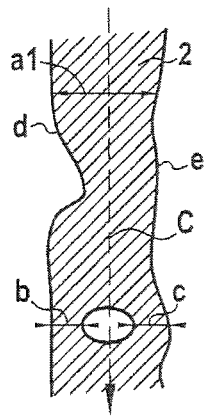
FIG.8
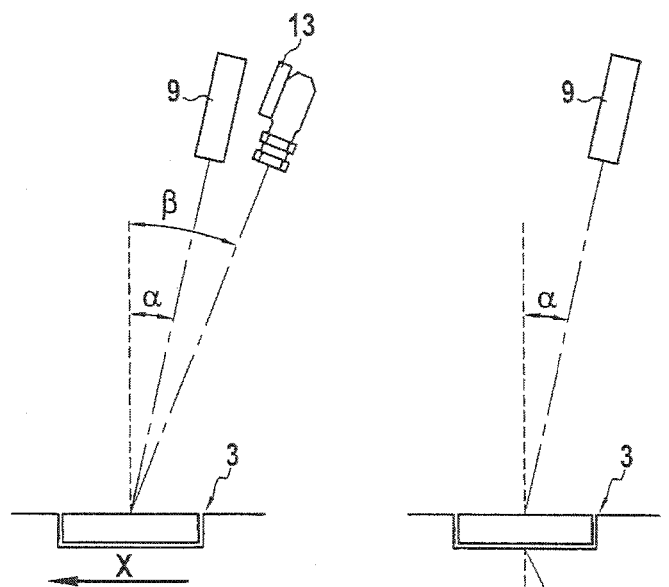
FIG.9   FIG.10
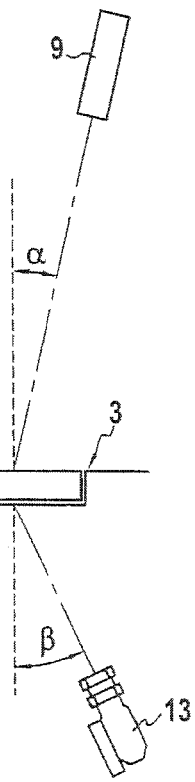

METHOD AND DEVICE FOR INSPECTING PACKAGING WELDS

The present invention relates to the technical field of inspecting packages that have been heat-sealed in the general sense.

The subject matter of the invention finds applications in particularly advantageous but non-exclusive manner in the field of inspecting packages for products in the agrifood, pharmaceutical, or cosmetics industries. The invention also applies to other packages such as pouches where two films are welded together.

In general manner, each heat-sealed package has at least one receptacle for receiving the product that is to be packaged. Each receptacle is closed by a film that is welded to the receptacle. The junction zone between the film and the receptacle corresponds to the weld that surrounds the receptacle and that is generally situated at the edge of the receptacle. The welds are in the form of strips defined by two opposite edges on either side of a guide curve.

After products have been packaged, it is necessary to verify the quality of the welding.

In the prior art, Document EP 2 350 621 describes methods making it possible to detect the presence of intrusions in the weld zone, which intrusions lead to a degradation firstly in the quality of the weld from a sealing point of view, and secondly in the attractiveness of the appearance associated with the product and the package. As a cause for weld failure, that solution serves only to detect the presence of contamination, and it does not make it possible to detect welding defects due to bubbles, due to regions that have not been welded, or due to colorless portions that are fatty or wet. In other words, the technique proposed is not sufficient to guarantee the quality of the welds. That solution is not satisfactory since it is found firstly that under certain welding process conditions, the quality of the welding does not provide a weld of sufficient width, which can lead to poor conservation of the product, even without any intrusions being present, and secondly, conversely, the presence of intrusions of small size does not endanger the conservation of the product so long as the width of the welding remains sufficient in spite of the presence of the intrusion. Furthermore, that technique is not suitable for detecting the presence of bubbles in the middle of the weld, even though that weakens the weld.

Patent application WO 2013/007951 describes a method of inspecting heat-sealed packaging structures in particular by using a linear image sensor. That method seeks to illuminate packages with a light beam that scans the welds in a scanning direction by extending transversely relative to the scanning direction.

That method seeks to act cyclically on each movement increment to acquire a sequence of n successive images, each obtained with a different exposure time and/or different lighting conditions.

Thereafter, that method seeks to group together image lines obtained in the sequences and having both the same exposure time and the same lighting conditions so as to obtain n superposable images that have been obtained with different exposure times and/or under different lighting conditions. The method seeks to analyze the images separately or in combination in order to determine at least one characteristic of the inspected packages.

That patent application describes a technique for inspecting packages that is simple and not onerous to implement, while being designed to make it possible to inspect an entire inspection zone even if it locally presents characteristics that are not uniform. Nevertheless, that document does not give any information about the method of analyzing the images in order to detect whether the packages have been welded correctly. Furthermore, the inspection technique described in that document does not make it possible to detect whether or not the packages are correctly welded.

U.S. Pat. No. 5,515,159 describes a vision system for inspecting packaging welds. That document makes provision for lighting the package with structured lighting making it possible to detect welds characterized by an imprint created by the coining effect during the sealing operation. That document also makes provision for using back-lighting in order to visualize welding defects.

That system also has a camera for obtaining an image of the package. The image is analyzed in such a manner as to determine the transverse width of the weld in order to determine whether the weld complies with a reference value.

That patent describes an inspection technique limited to welds including an imprint due to the coining during the heat-sealing operation. Furthermore, the inspection technique described in that patent does not make it possible to obtain an image of welds with sufficient accuracy to determine whether or not the packages are correctly welded.

The present invention thus seeks to remedy the drawbacks of the prior art by proposing a technique that makes it possible to inspect welds presented by heat-sealed packages by detecting with great accuracy portions that are welded or not welded, so as to reveal all portions that are not welded and measure accurately the width of the welding, with this taking place all along the guide curve of the welds so as to determine whether the packages are defective or correctly welded.

Another object of the invention is to inspect the quality of packaging welds by an optical method that operates through a transparent or translucent portion and that provides the advantage of inspecting at a speed that matches the fabrication method and that does not have any direct contact with the package.

To achieve this object, the invention provides a method of inspecting welds of packages, said welds being in the form of respective strips defined by two opposite edges on either side of a guide curve, the method consisting in:

scanning the welds in a scanning direction by means of a light beam supplied by a light source illuminating the packages, said beam extending transversely to the direction in such a manner as to cover a field width;

acquiring at each of N successive scanning increments a raw matrix image of the illuminated packages by using a camera having a lens and having a rectangular field at least of dimension in the scanning direction and at least of the inspection width in the direction orthogonal thereto; and analyzing the images supplied by the camera.

According to the invention, the following steps are performed:

creating a light beam that produces at least one light transition in the scanning direction on the package, the transition extending over the field width;

acquiring a raw matrix image covering the light transition;

for each image obtained, extracting over the entire field width a measurement of the diffusion of the light transition as imparted by the package, and storing these measurements;

for each of N successive scanning increments, using the raw matrix image to create an image line of width in which each pixel receives as its value the measurement in the raw matrix image of the diffusion of at least the light transition;

stores at least image lines in succession to obtain by juxtaposition a matrix image, the image containing at least the two opposite edges of the weld for at least a fraction of the guide curve, and storing the image; and analyzing the matrix image:

by identifying the pixels belonging to the weld by means of their values;

by determining at least the transverse width as a characteristic of the weld at all points along the fraction of the guide curve; and by determining that the weld along said fraction is in conformity when its transverse width remains, at all points, greater than a given minimum.

The method of the invention also includes in combination one and/or more of the following additional characteristics:

during the segmentation step:

pixels having diffusion values lying in a determined range are preselected as potentially belonging to the weld; and in the vicinity of the guide curve, a set of connected pixels is selected from the preselected pixels so that together they constitute the weld;

measuring the diffusion of the transition in the raw matrix image by taking account of the spread of the transition, which spread is characterized either by a drop in the light gradient in the vicinity of the transition, or by a shift of a point at which a defined light threshold is crossed, or by measuring the gray levels of pixels along selected lines situated outside the illuminated zone, but in the vicinity of the light transition;

a strip of light is projected as the light beam, which strip of light produces two light transitions in the field of the camera, and diffusion is measured by analyzing the two transitions;

a narrow strip of light is projected as the light beam, which strip of light is of cross-section that corresponds to a light peak;

diffusion is measured by the spreading of the determined light peak, either by the width between two points crossing a defined light threshold, or by the drop in the height of the peak, or by measuring the gray levels of pixels considered along selected lines situated on either side of the illuminated zone, outside but close to the light transition, or by the drop in the light gradient in the vicinity of the transition;

analyzing the image solely for an inspection zone of area that is much smaller than the area of the image but covering at least the weld that is considered as being correct, said inspection zone being a region that is geometrically defined beforehand and that is positioned in the image either as a function of a priori knowledge of the positions of packages during inspection, or as a function of the results of a step of locating the weld by analyzing the image;

analyzing the image as soon as scanning obtains an image containing at least the two opposite edges of the weld for at least a fraction of the guide curve;

selecting the angle of incidence with which the light beam is projected and the angle of observation of the camera defined as the angle between its optical axis and the normal to the surface of the package in such a manner as to avoid acquiring light that is reflected in specular manner by the package; and selecting the angle of incidence with which the light beam is projected and the angle of observation of the camera defined as the angle between its optical axis and the normal to the surface of the package in such a manner as to limit eliminate masking of the weld by the edges of the receptacles of the packages.

The invention also proposes a device for inspecting welds of packages, said welds being in the form of respective strips defined by two opposite edges on either side of a guide curve, the device comprising:

a light source illuminating the packages with a light beam extending in a direction in such a manner as to cover a field width;

a camera provided with a lens and having a rectangular field at least of the inspection width in the direction and at least of dimension in the direction orthogonal thereto suitable for providing a raw matrix image of the illuminated packages;

means for scanning the welds by the light beam and the rectangular field of the camera in a direction transverse to the direction; and a processor unit for processing the successive raw matrix images delivered by the camera during at least N scanning increments.

According to the invention:

the light beam produces at least one light transition in the scanning direction of the package, the light transition extending over the field width;

and, for each of the N successive scanning increments, the processor unit:

acquires a raw matrix image covering the light transition(s);

extracts from each image over the entire field width a measurement of the diffusion of the light transition imparted by the package, and then stores the measurement;

for each of the N successive scanning increments, uses the raw matrix image to create an image line of width in which each pixel receives as its value the measurement in the raw matrix image of the diffusion of the light transition(s);

stores at least N image lines in succession to obtain by juxtaposition a matrix image containing at least the two opposite edges of the weld for at least a fraction of the guide curve, and stores it;

identifies in the matrix image the pixels belonging to the weld by means of their values;

determines at least its transverse width as a characteristic of the weld at all points along the guide curve; and determines that the weld is in compliance over said portion when its transverse width remains at all points greater than a given minimum.

The device of the invention may also include in combination one or more of the following additional characteristics:

the light beam produces a strip of light on the package that presents, in the field of the camera, two light transitions extending over the entire field width;

the light beam produces a narrow line of light extending on the package over the entire field width and presenting a peak in the direction that lies between two close-together light transitions;

the system for scanning the welds by the light beam and by the rectangular field of the camera comprises means for moving the packages in translation through the field of the camera, or for advancing them in jerks;

the system for scanning the welds by the light beam and by the rectangular field of the camera comprises means for moving optical devices relative to the packages, which are stationary or advance in jerks;

the system for scanning the welds by the light beam and by the rectangular field of the camera comprise optical devices for deflecting light rays from the source and light rays picked up by the camera, said optical devices being interposed between the packages on one side and the light source of the camera on the other;

the scanning system delivers information to the processor unit about the positions of the packages relative to the field of the camera;

the angle of incidence with which the light beam is projected and the angle of observation of the camera defined as the angle between its optical axis and the normal to the surface of the package are selected in such a manner as to avoid acquiring light that has been reflected or transmitted in specular manner by the package;

the light source and the camera are situated on the same side of the package, the angle of incidence with which the light beam(s) is/are projected and the angle of observation of the camera defined as being the angle between its optical axis and the normal to the surface of the package are selected to lie in the range 10° to 30°, and preferably in the range 20° to 25°; and the angle of incidence with which the light beam is projected is selected to lie in the range 5° to 30° and preferably in the range 15° to 20°, while the angle of incidence of observation by the camera defined as the angle between its optical axis and the normal to the surface of the package lies in the range 0° to 5° and is preferably equal to 0°, the source and the camera being situated in opposite manner relative to the package.

The invention thus consists in inspecting the assembled zone constituted by two welded-together films (receptacle and top film) by analyzing the properties of light diffusion in the welded zone, i.e. by analyzing light that has been reflected or transmitted in non-specular manner by the package.

The object of the invention is to determine the zone in which welding has really taken place and in measuring its width. For this purpose, the invention relies on the way the light diffusion properties of the materials used for fabricating packages are modified as a result of welding (heating the material and welding together the two superposed films). This property modification is used by the invention to determine the zones that have really been welded.

Various other characteristics appear from the following description made with reference to the accompanying drawings, which show embodiments of the invention by way of non-limiting examples.

FIG. 1 is a view of an example of a device in accordance with the invention for inspecting packaging welds, in a reflection setup.

FIG. 2 is a view from beneath of a package to be inspected.

FIG. 3 shows an example of a raw matrix image B(N) of a portion of a package including a weld.

FIG. 3A plots gray level curves extending in the scanning direction at two characteristic points of the inspection direction.

Figure 4A:
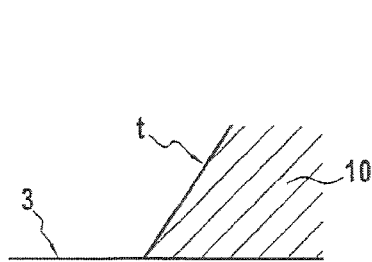

FIG. 4A is a view of a light beam implemented in the form of a strip of light producing a light transition for illuminating a package.

Figure 4B:
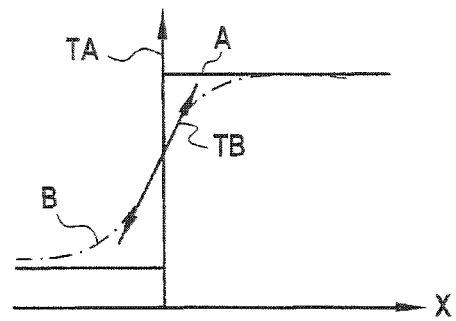

FIG. 4B shows the gray level in the scanning direction for a light transition with diffusion and with little diffusion.

Figure 5A:
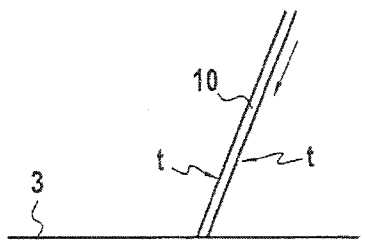

FIG. 5A is a view of a light implemented in the form of a strip of light producing two light transitions for illuminating a package.

Figure 5B:
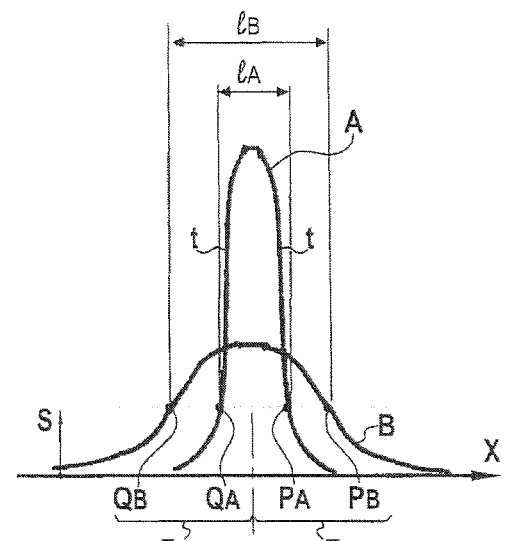
Figure 5C:
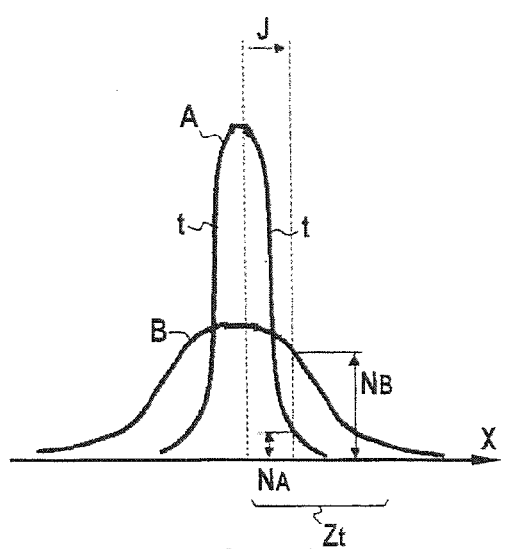
Figure 5D:
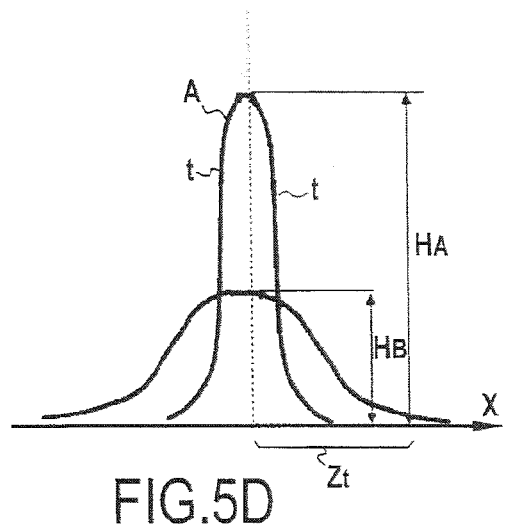

FIGS. 5B, 5C, and 5D are diagrams showing the gray levels in the scanning direction for light transitions with diffusion and with little diffusion, making it possible to measure diffusion using three different methods.

FIG. 6 shows an example of an image line I(N) obtained from diffusion values extracted from a raw matrix image B(N) as shown in FIG. 3.

FIGS. 7A and 7B are examples of matrix images I containing a portion of the package in which a fraction of the weld appears.

FIG. 8 is a diagram illustrating the concept of the transverse width of the weld.

FIG. 9 shows another reflection setup variant for the device of the invention in which the camera and the light source are arranged on the same side of the package.

FIG. 10 shows another setup variant for the device of the invention operating in transmission with the camera and the light source arranged on opposite sides of the package.

Figure 11:
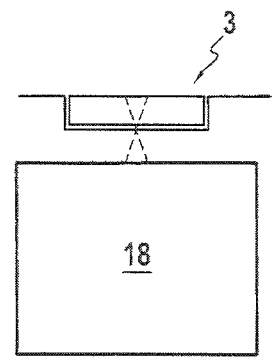

FIG. 11 is an optical diagram for inspecting a package with a deep receptacle.

Figure 12:
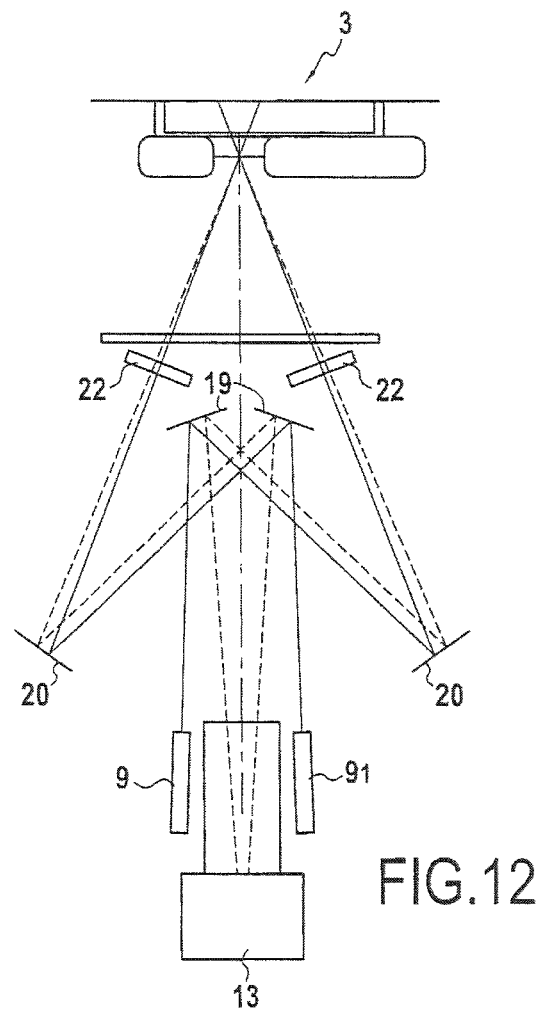

FIG. 12 shows an embodiment of the optical setup of FIG. 11.

As can be seen more clearly in FIGS. 1 and 2, the subject matter of the invention relates to a device 1 for inspecting the welds 2 of heat-sealed packages 3 in order to determine whether or not the welds are in compliance. In the preferred application shown in the drawings, each heat-sealed package 3 includes a receptacle 4 for receiving a product and each receptacle 4 is closed by a film 5 that is fastened on the receptacle by a weld 2. In a preferred application, the package 3 is for packaging products in the agrifood industry, but it is clear that the inspection device of the invention can be applied to packages relating to other industries.

In the example shown in FIG. 2, the weld 2 presents a geometrical shape that is substantially rectangular, however it is clear that the invention applies to inspecting welds presenting other shapes. In general manner, a weld 2 is considered to be a strip or band defined by two opposite edges d, e situated on either side of a guide curve C along which the weld extends.

The inspection device 1 also has at least one light source 9 illuminating the packages 3 with a light beam 10 extending in an inspection direction Y so as to cover a field of width L in which the welds 2 for inspection are situated. In accordance with the invention, the light beam 10 produces, on the package 3 in a scanning direction X at least one, and in the example shown in FIG. 2, two light transitions t that extend along the field width L. In this embodiment, the light beam 10 forms a strip of light producing two light transitions t extending along the field width L.

In an advantageous embodiment, the light beam 10 produces a narrow line of light extending along the entire field width L and presenting a peak in the scanning direction X that lies between two close-together light transitions. The term "light transition" t should be understood as a rapid change in light level, more precisely in the illumination produced in the direction X. In other words, the illumination function along the direction X tends towards a step type function. For example, the light source 9 is an anamorphic laser or focused lighting based on light-emitting diode (LED) technology.

The inspection device 1 also has a camera 13 with a lens 14 presenting a rectangular field of dimensions L×H, where L corresponds to the width of inspection of the package in the direction Y, and a dimension H extending in a direction perpendicular to the inspection direction Y. The images acquired by the camera are transmitted to an image processor unit 15 that is described in detail in the description below.

The inspection device 1 also has a system 16 for scanning the welds 2 by the light beam 10 and the rectangular field of the camera 13 in the scanning direction X. It should be understood that such a scanning system 16 serves to illuminate the welds 2 (by the beam 10) and to take images (by the camera 13) of the illuminated welds 2, and to do so for all of the welds of the packages. It should be observed that in the example shown in FIG. 2, the scanning direction X is perpendicular to the inspection direction Y since the X, Y, Z reference frame is orthonormal. Nevertheless, in general manner, the scanning direction X extends transversely relative to the inspection direction Y so as to make it possible to cover all of the weld by means of the beam 10 and the field of the camera.

In an embodiment, the scanning system 16 for scanning the welds 2 with the light beam 10 and the rectangular L×H field of the camera 13 comprise means for moving the packages continuously or in jerks in translation in the field of the camera 13. In other words, the camera 13 is stationary and may be placed at the outlet from the package fabrication line where the packages are conventionally moved in translation by a conveyor. For example, the receptacles are connected together and the strip of film and the receptacles are cut apart prior to inspection. The packages are thus caused to travel past an inspection station either continuously on a conveyor line, or in jerks corresponding to the operation of a packaging machine.

In another embodiment, the distance system 16 for scanning the welds 2 by the light beam 10 and the rectangular field L×H of the camera 13 comprise means for moving optical devices relative to stationary packages, or for advancing them in jerks.

In yet another embodiment, the system 16 for scanning the welds 2 by the light beam 10 and the rectangular L×H field of the camera 13 comprise optical devices for deflecting light rays from the light source 9 and light rays picked up by the camera 13, said optical devices being interposed between the packages on one side and the light source 9 of the camera 13 on the other.

In yet another embodiment, the scanning system 16 delivers information to the processor unit 15 about the position of the packages 3 relative to the field of the camera.

It should be observed that it is considered that the scanning system 16 performs N scanning increments in order to inspect all of the welds 2 of a package 3.

Thus, the camera 13 delivers raw matrix images B(N) for each scanning increment N. Naturally, each raw matrix image B(N) covers the light transition(s) t. FIG. 3 shows an example of a raw matrix image B(N) of a portion of a package including a weld 2. This raw matrix image B(N) contains two light transitions t formed by a line of light and it presents a rectangular field of dimensions L×H, where L corresponds to the inspection length of the package in the direction Y and where a dimension H extends along the scanning direction X, which is transverse to the inspection direction Y.

The raw matrix images B(N) that are delivered successively by the camera 13 during the N increments are acquired and processed by the processor unit 15. The processor unit 15 has means for performing the method in accordance with the invention as described in greater detail in the description below. This processor unit 15 also has means for storing data, as can be seen from the description below.

In accordance with the invention, the method consists, for each acquired image B(N), in extracting across the entire field width L a measurement of the diffusion imparted by the package to the light transition t, or as in the example shown, the diffusion imparted to both light transitions t. These measurements of the diffusion imparted by the package of the light transitions t are stored.

The method of the invention thus makes use of the differences in the light diffusion property in the package, which differences are specific to the welded zones or welds 2 as contrasted with the non-welded zones. For a given type of packaging material, the material in a non-welded zone diffuses light little, and light does not propagate in the thickness of the material at the interface between the film and the receptacle. For this type of material, the material of the welded portion conversely diffuses to a greater extent and in particular light propagates and then diffuses within the welded portion.

In FIG. 3, there can be seen a zone $Z_1$ of little light diffusion corresponding to a non-welded portion of the package, and a zone $Z_2$ of stronger light diffusion corresponding to a welded portion of the package. FIG. 3A shows an example of a curve obtained from the raw matrix image shown in FIG. 3 and giving gray level curves that extend in the scanning direction X. The gray level curve A of camera pixels taken at a point $A_1$ across the field width L is situated in the zone $Z_1$, while the gray level curve B taken at a point $B_1$, which is different from the point $A_1$, is situated in the zone $Z_2$.

It can thus be considered that the light diffusion zones (i.e. the zone $Z_2$ in the example shown in FIG. 3) are welded zones such that by analyzing these zones, the welded zones can be measured. Nevertheless, for other types of packaging material, it is found that the diffusion properties are inverted, i.e. the material of a welded portion diffuses little.

The diffusion that is imparted by the package to the light transition t in the raw matrix image B(N) is measured by the spread of the light transition(s) t. This spread may be characterized in various ways, such as for example by a drop in the light gradient in the vicinity of the transition (FIGS. 4A, 4B), by a shift of a point (PA to PB) where a defined light threshold is crossed (FIGS. 5A, 5B), or by measuring the gray levels of the pixels considered along selected lines situated outside the illuminated zone, but in the vicinity of the light transition (FIG. 5C), or by measuring the gray level of the peak of the gray level values (FIG. 5D).

In the example shown in FIGS. 4A and 4B, the light beam 10 is a strip of light producing a light transition t in the field L×H of the camera. The diffusion is measured by analyzing this light transition t of the strip of light. FIG. 4B shows the gray levels of the pixels of the camera in the scanning direction X for the light transition t presenting little diffusion (curve A) and presenting diffusion (curve B). Curve A with little diffusion presents a slope TA at the transition, whereas curve B that presents diffusion possesses a slope TB of value smaller than the slope TA. Diffusion measurement can thus be characterized by the light gradient in the vicinity of the transition, i.e. by the slope of gray levels. The lower the slope, the greater the amount of diffusion.

In a preferred embodiment shown in FIGS. 5A, 5B, 5C, and 5D, the light beam 10 is a narrow line of light producing two light transitions t in the field L×H of the camera (FIG.

5A). The term "narrow line of light" is used to mean that the line of light is of a width such that attenuation appears in the peak gray level when the light is diffused inside the material. Diffusion is measured by analyzing this line of light, or at least one transition t.

FIG. 5B shows the gray level in the scanning direction X for light transitions t presenting little diffusion (curve A) and presenting diffusion (curve B). For a light threshold value S, the curve A with little diffusion presents two transition points PA and QA where the threshold S is crossed that are spaced apart from each other by a width lA, whereas the curve B with diffusion presents two transition points PB and QB at the locations where the threshold S is crossed that are spaced apart from each other with a width lB that is greater than the width lA. In this variant, the width lA or lB measures diffusion. The greater this width, then the greater the amount of diffusion. It should be observed that in the example shown, the width is taken over the luminous zones Zt of the two light transitions t. Naturally, it could also be taken over the width of a single light transition corresponding to a half width lA or lB, to the distance between the transition points PB, PA or QA, QB and a reference, such as for example the middle of the line of light.

In the embodiment shown in FIG. 5C, diffusion is measured by measuring gray level along a selected line J taken at a given location in the scanning direction X. For this line J, the gray level NA for a curve A presenting little diffusion is lower than the gray level NB of a curve B presenting a large amount of diffusion. It should be observed that it is possible to position the line J in such a manner that the level NA is zero, i.e. along selected lines that are situated outside the illuminated zone, but in the vicinity of the light transition. In this variant embodiment shown in FIG. 5C, the gray levels NA, NB characterize the diffusion of the transition t. It is possible to perform the same analysis along a line that is symmetrical to J relative to the peaks, and to take into account a combination of levels over both lines on either side of the line of light. In this variant, the gray level NA, NB is a measure of the diffusion. The higher the gray level, the greater the amount of diffusion.

In the element shown in FIG. 5D, diffusion is measured by measuring the gray level at the peak of the gray level values. The gray level of the peak HA of a curve A presenting little diffusion is higher than the gray level HB of the peak of a curve B presenting a large amount of diffusion. The gray level of the peak may advantageously be taken as the maximum value of gray level found when searching in the scanning direction X. The lower gray level peak is characteristic of diffusion. The lower the peak, the greater the amount of diffusion. The ratio of the peak levels or the difference between the peak levels is also characteristic of diffusion.

As described above, the method of the invention thus consists in acting on each raw matrix image B(N) and over the entire width L of the field to extract the measurements of diffusion for each package in the light transition(s) as obtained using one or another of the above-described methods, and to store those measurements. Thus, by way of example, it is possible, in the inspection direction Y, to obtain a diffusion function that, on the principles described above, may be expressed as follows: l(y), N(y), HA-HB(y) or P(y).

Thereafter, for each of N successive scanning increments, the method of the invention consists in using the raw matrix image B(N) to create an image line I(N) of width L in which each pixel receives as its value the measurement of the diffusion of the light transition(s) in the raw matrix image B(N). FIG. 6 is an example of an image line I(N) obtained from diffusion values extracted from the raw matrix image B(N) shown in FIG. 3.

The method of the invention then consists in storing N image lines I(N) one after another so as to obtain, by juxtaposition, a matrix image I containing at least the two opposite edges d, e of the weld for at least a fraction of the guide curve C. FIGS. 7A and 7B are example of matrix images I containing a portion of the package in which a fraction of the weld 2 can be seen. It should be observed that in the example shown in FIG. 7A, the weld 2 appears to be dark whereas in the example shown in FIG. 7B, the weld appears to be pale.

The method of the invention then consists in analyzing the matrix image I in order to determine whether the weld is or is not correct. For this purpose, the matrix image I is analyzed by:
  identifying the pixels that form part of the weld 2 by using their values;
  determining at least the transverse width a at all points along the fraction of the guide curve C, this width constituting a first characteristic of the weld; and
  determining that the weld 2 over said fraction is in compliance so long as its transverse width a remains, at all points, greater than a given minimum.

The minimum thickness corresponds to the limit value below which it is considered that the width of the weld is not sufficient for providing correct packaging. Thus, if the thickness of the weld 2 at all points is greater than this minimum value, then the weld 2 of the packaging is considered as being correct. Conversely, if the thickness of the weld 2 is less than this minimum value, then the weld 2 of the packaging is considered as being defective.

FIG. 8 shows the concept of the transverse width of the weld 2. The transverse width a of the weld 2 in a first variant is used to mean the width $a_1$ of the weld strip as measured perpendicularly to the guide curve C at all points along the strip.

Among potential causes of failure to weld, there is the presence of bubbles, which do not necessarily occur at the edge of the weld, but which may be found in the middle. To take defects of this type into account, in another variant, the transverse width a of the weld is the accumulated transverse width a=b+c. This width is easily generalized by taking account of the number of pixels forming part of the weld and considered in an inspection zone placed on the weld.

These pixel measurements may be obtained by any method taken from image processing techniques such as counting pixels that are connected or not connected along segments that are orthogonal to the guide curve C, or by detecting outlines and measuring distances between outlines.

Typically, the processing of the matrix image I for the purpose of identifying pixels that belong to the weld 2 because of their values is performed during a step of segmenting the image, which step consists in:
  preselecting pixels having diffusion values lying in a determined range as potentially belonging to the weld 2; and
  selecting in the vicinity of the guide curve C a set of connected pixels from the preselected pixels for the purpose of constituting the set of pixels that belong to the weld.

In an advantageous variant implementation, analysis of the image I begins as soon as scanning has obtained an image I that contains at least two opposite edges d, e of the weld for at least a fraction of the guide curve C.

In another advantageous variant implementation, the image I is analyzed only for an inspection zone of area that is much smaller than the image I, but that covers at least the weld 2 that is considered as being correct. This inspection zone is a region that is geometrically defined beforehand and that is positioned in the image I, either as a function of a priori knowledge of the positions of packages during inspection, or else as a function of the results of a step of locating the weld by analyzing the image I.

It follows from the above description that the subject matter of the invention seeks to inspect the quality of welds by analyzing the diffusion properties of light reflected or transmitted by the package. Thus, the angle of incidence α with which the light beam 10 is projected and the angle of observation β of the camera defined as the angle between its optical axis and the normal to the surface of the package, are both selected in such a way as to avoid acquiring light that is reflected or transmitted in specular manner by the package.

Likewise, the angle of incidence α with which the light beam is projected and the observation angle β of the camera defined as the angle between its optical axis and the normal to the surface of the package, are both selected in such a manner as to limit or indeed eliminate the weld being hidden by the edges of the receptacles in the packages.

FIGS. 1 and 9 show two variant setups for the device of the invention operating in reflection in which the camera 13 and the light source 9 are both on the same side of the package 3. In the embodiment shown in FIG. 1, the camera 13 and the light source 9 are on the same side as the receptacle 4 of the package 3. This setup is particularly suitable for a package of small thickness presenting an opaque film that might be printed over the weld. In the example shown in FIG. 9, the camera 13 and the light source 9 are on the side opposite from the receptacle 4 of the package 3. This setup is particularly suitable for a package of arbitrary thickness presenting a translucent film with uniform printing over the weld.

In these reflection setups, the light source 9 is positioned so that the angle of incidence α with which the light beam 10 is projected, as measured relative to the normal to the plane of the film of the package, lies in the range 10° to 30° and preferably in the range 20° to 25°, while the angle of observation β of the camera 13 defined as the angle between its optical axis and the normal to the surface of the package lies in the range 10° to 30°, and preferably in the range 20° to 25°. These angles are selected in this way for the following reasons:

they have the same sign (in other words the camera and the source are both on the same side to the normal to the receptacle) so that the camera lies outside the specular reflection axis of the laser. Otherwise reflections would appear; and they are preferably greater than 20° so as to remain far away from the specular domain even if the edge of the package slopes a little or is slightly deformed. Assuming that the film is never deformed (which should theoretically be true within the packaging machine), these two angles may advantageously be reduced to values that are strictly positive (or respectively strictly negative).

FIG. 10 shows another setup variant for the device of the invention that operates in transmission, in which the camera 13 and the light source 9 are arranged on opposite sides of the package 3, with the camera situated beside the receptacle 4. For transmission setups, the light source 9 is positioned so that the angle of incidence α with which the light beam 10 is projected as measured relative to the normal to the plane of the packaging film lies in the range 5° to 30°, and preferably in the range 15° to 20°, whereas the observation angle β of the camera 13, defined as the angle between its optical axis and the normal to the surface of the package lies in the range 0° to 5° and is preferably equal to 0°. These angles are selected for the following reasons:

the camera angle is preferably zero in order to be able to observe the front and the rear of the package at the same angle of incidence. A non-zero angle would lead to the welds situated at the front of the package (or at the rear) being hidden by the front (or rear) edge of the bottom of the package; and the angle of the light source is a compromise between:
if the angle is smaller (e.g. in the range 0° to 15°), the light beam is emitted directly at the camera and dazzles it; and if the angle is larger (e.g. greater than 20°) the laser illuminates the vertical flank at the rear of the package, which can give rise to reflections or "hot points" in the weld.

From the above description, it can be seen that the light beam 10 advantageously possesses a spectral composition that is suitable for passing through the material of the package. Likewise, the light beam 10 possesses a spectral composition that is suitable for being strongly absorbed by at least one specific type of intrusion.

FIGS. 11 and 12 show a variant embodiment of the invention enabling welds to be inspected that are made more particularly on packages 3 that are of a shape in which the relative height of the tray and the position of the weld do not enable the weld to be observed at the observation angle β of the camera 13. With such packages, a zone that is masked from the camera appears for the portion of the package that is situated low down in front of the face 23 (FIG. 1), whereas the portion of the package that is situated low down and behind the face 24 (FIG. 1) is visible.

In this variant embodiment, the device of the invention has an optical sensor 18 interposed between the packages 3 on one side and the camera 13 and two light sources 9, 9$_1$ on the other. The optical system 18 is designed so that both the angles of incidence at which the light beams from the two light sources 9 and 9$_1$ are projected, and also the angles of observation of the camera, are symmetrical about the normal to the package. Using such an optical setup makes it possible to observe the package 3 along two symmetrical observation axes, thus enabling masked zones to be eliminated.

Naturally, numerous embodiments could be envisaged for implementing such an optical setup. FIG. 12 shows an embodiment of a setup in which the light sources 9, 9$_1$, such as laser diodes are situated on either side of the camera 13. In the embodiment shown in FIG. 12, the optical system 18 comprises a first set of symmetrical mirrors 19 placed facing the light sources 9, 9$_1$ and the camera 13, and positioned so as to reflect light beams towards a second set of symmetrical mirrors 20 arranged to illuminate and observe the package 3 in symmetrical manner about the normal to the package. A lens 22 is positioned on each of the light paths of the beams between the mirrors 20 of the second set and the package 3.

Naturally, the light beams that illuminate the package present all of the characteristics of the light beam 10 as described above. Thus, each light beam extends transversely to the scanning direction X and produces at least one light transition t extending on the package 3 in the scanning direction over the field width L. Furthermore, the light sources 9, 9$_1$ are switched on and off by a control unit that causes either both light sources to be on simultaneously, or that causes the two sources to operate in alternation over respective half-lengths of the package considered in the scanning direction. The camera 13 serves to reconstruct two images corresponding to observing the package along different optical paths over at least its half-lengths.

It should be observed that in the mode of operating both light sources simultaneously, the camera 13 can reconstruct two complete images of the observed package at two symmetrical angles of observation. The image processor unit then makes use only of the portion of each observed image that is not masked. In the mode of operating the light sources in alternation, the camera acts during each illumination to reconstruct an image corresponding to non-masked half of the observed package. The processor unit 15 serves to process the images with the above-described method.

The invention is not limited to the examples that are described and shown since various modifications may be made thereto without going beyond the ambit of the invention.

The invention claimed is:

1. A method of inspecting welds of packages, said welds being in the form of respective strips defined by two opposite edges on either side of a guide curve, the method consisting in:
   scanning the welds in a scanning direction by means of a light beam supplied by a light source illuminating the packages, said beam extending transversely to the scanning direction in such a manner as to cover a field width (L);
   acquiring at each of N successive scanning increments a raw matrix image of the illuminated packages by using a camera having a lens and having a rectangular field (L×H) at least of dimension (H) in the scanning direction and at least of the field width in the direction orthogonal thereto; and
   the method being characterized by the following steps:
   creating a light beam that produces at least one light transition in the scanning direction on the package, the transition extending over the field width;
   acquiring a raw matrix image covering the light transition;
   for each raw matrix image obtained, extracting over the entire field width a measurement of the diffusion of the light transition as imparted by the package, and storing these measurements;
   for each of N successive scanning increments, using the raw matrix image to create an image line of width L in which each pixel receives as its value the measurement in the raw matrix image of the diffusion of at least the light transition;
   storing at least N image lines in succession to obtain by juxtaposition a matrix image, the image containing at least the two opposite edges of the welds for at least a fraction of the guide curve, and storing the image; and
   analyzing the matrix image:
      by identifying the pixels belonging to the welds by means of their values;
      by determining at least a transverse width of the welds as a characteristic of the welds at all points along the fraction of the guide curve; and
      by determining that the welds along said fraction are in conformity when the transverse width remains, at all points, greater than a given minimum.

2. A method according to claim 1, characterized in that during a segmentation step:
   pixels having diffusion values lying in a determined range are preselected as potentially belonging to the welds; and
   in the vicinity of the guide curve, a set of connected pixels is selected from the preselected pixels so that together they constitute the welds.

3. A method according to claim 1, characterized in that it consists in measuring the diffusion of the transition in the raw matrix image by taking account of the spread of the transition, which spread is characterized either by a drop in the light gradient in the vicinity of the transition, or by a shift of a point at which a defined light threshold is crossed, or by measuring the gray levels of pixels along selected lines situated outside a zone illuminated by the light beam, but in the vicinity of the light transition.

4. A method according to claim 1, characterized in that a strip of light is projected as the light beam, which strip of light produces two light transitions in the rectangular field of the camera, and diffusion is measured by analyzing the two transitions.

5. A method according to claim 1, characterized in that a narrow strip of light is projected as the light beam, which strip of light is of cross-section that corresponds to a light peak.

6. A method according to claim 5, characterized in that diffusion is measured by the spreading of the light peak, either by the width between two points crossing a defined light threshold, or by the drop in the height of the light peak, or by measuring the gray levels of pixels considered along selected lines situated on either side of a zone illuminated by the light beam, outside but close to the light transition, or by the drop in the light gradient in the vicinity of the transition.

7. A method according to claim 1, characterized in that it consists in analyzing the matrix image solely for an inspection zone of area that is much smaller than the area of the matrix image but covering at least the welds that is considered as being correct, said inspection zone being a region that is geometrically defined beforehand and that is positioned in the matrix image either as a function of a priori knowledge of the positions of packages during inspection, or as a function of the results of a step of locating the welds by analyzing the matrix image.

8. A method according to claim 1, characterized in that it comprises analyzing the matrix image as soon as juxtaposition of N image lines, created using the raw matrix image for each of N successive scanning increments, obtains an image containing at least the two opposite edges of the welds for at least a fraction of the guide curve.

9. A method according to claim 1, characterized in that it consists in selecting the angle of incidence with which the light beam is projected and the angle of observation of the camera defined as the angle between its optical axis and the normal to the surface of the package in such a manner as to avoid acquiring light that is reflected in specular manner by the package.

10. A method according to claim 1, characterized in that it consists in selecting the angle of incidence with which the light beam is projected and the angle of observation of the camera defined as the angle between its optical axis and the normal to the surface of the package in such a manner as to limit eliminate masking of the welds by the edges of the receptacles of the packages.

11. A device for inspecting welds of packages, said welds being in the form of respective strips defined by two opposite edges on either side of a guide curve, the device comprising:

a light source illuminating the packages with a light beam extending in a direction (Y) in such a manner as to cover a field width (L);

a camera provided with a lens and having a rectangular field (L×H) at least of the field width in the direction Y and at least of dimension (H) in the direction orthogonal thereto suitable for providing raw matrix images of the illuminated packages;

a system for scanning the welds by the light beam and the rectangular field (L×H) of the camera in a scanning direction transverse to the direction Y; and a processor unit for processing the successive raw matrix images delivered by the camera during at least N successive scanning increments;

the device being characterized in that:

the light beam produces at least one light transition in the scanning direction of the package, the light transition extending over the field width;

and in that, for each of the at least N successive scanning increments, the processor unit:

acquires a raw matrix image covering the light transition;

extracts from each raw matrix image over the entire field width a measurement of the diffusion by the package of the light transition, and then stores the measurement;

for each of the N successive scanning increments, uses the raw matrix image to create an image line of width L in which each pixel receives as its value the measurement in the raw matrix image of the diffusion of the light transition(s);

stores at least N image lines in succession to obtain by juxtaposition a matrix image containing at least the two opposite edges of the welds for at least a fraction of the guide curve, and stores it;

identifies in the matrix image the pixels belonging to the welds by means of their values;

determines at least a transverse width of the welds as a characteristic of the welds at all points along the guide curve; and determines that the welds are in compliance over said portion when the transverse width remains at all points greater than a given minimum.

12. A device according to claim 11, characterized in that it includes an optical system interposed between the packages on one side and the camera and two light sources on the other side in such a manner as to ensure firstly that the angles of incidence with which the light beams are projected from the two sources and secondly the angles of observation of the camera are symmetrical about the normal to the package.

13. A device according to claim 12, characterized in that the light sources are subjected to on/off control that either causes the two sources to operate simultaneously, or else causes the two sources to operate in alternation over the half-length of the package considered in the scanning direction, the camera serving to reconstruct two images corresponding to observation of the package along different light paths, at least in its half-lengths.

14. A device according to claim 11, characterized in that each light beam produces a strip of light on the package that presents, in the field of the camera, two light transitions extending over the entire field width.

15. A device according to claim 11, characterized in that each light beam produces a narrow line of light extending on the package over the entire field width and presenting a peak in the scanning direction that lies between two close-together light transitions.

16. A device according to claim 11, characterized in that the system for scanning the welds by the light beam and by the rectangular field of the camera comprises means for moving the packages in translation through the field of the camera, or for advancing them in jerks.

17. A device according to claim 11, characterized in that the system for scanning the welds by the light beam and by the rectangular field of the camera comprises movable optical devices relative to the packages, which are stationary or advance in jerks.

18. A device according to claim 11, characterized in that the system for scanning the welds by the light beam and by the rectangular field of the camera comprise optical devices for deflecting light rays from the source and light rays picked up by the camera, said optical devices being interposed between the packages on one side and the light source of the camera on the other.

19. A device according to claim 11, characterized in that the system for scanning delivers information to the processor unit about the positions of the packages relative to the field of the camera.

20. A device according to claim 11, characterized in that the angle of incidence with which each light beam is projected and the angle of observation of the camera defined as the angle between its optical axis and the normal to the surface of the package are selected in such a manner as to avoid acquiring light that has been reflected or transmitted in specular manner by the package.

21. A device according to claim 11, characterized in that the light source and the camera are situated on the same side of the package, the angle of incidence with which the light beam is projected and the angle of observation of the camera defined as being the angle between its optical axis and the normal to the surface of the package are selected to lie in the range 10° to 30°, and preferably in the range 20° to 25°.

22. A device according to claim 11, characterized in that the angle of incidence with which the light beam is projected is selected to lie in the range 5° to 30° and preferably in the range 15° to 20° while the angle of observation by the camera defined as the angle between its optical axis and the normal to the surface of the package lies in the range 0° to 5° and is preferably equal to 0°, the source and the camera being situated in opposite manner relative to the package.

* * * * *